United States Patent [19]

Yazaki et al.

[11] Patent Number: 4,977,157

[45] Date of Patent: Dec. 11, 1990

[54] AQUEOUS PREPARATION OF 9-METHYL-3-(1H-TETRAZOL-5-YL)-4H-PYRIDO[1,2-A])PYRIMIDIN-4-ONE POTASSIUM SALT

[75] Inventors: Takashi Yazaki; Kazunori Takuma, both of Misato, Japan

[73] Assignee: Tokyo Tanabe Company, Ltd., Tokyo, Japan

[21] Appl. No.: 264,439

[22] Filed: Oct. 27, 1988

[30] Foreign Application Priority Data

Nov. 10, 1987 [JP] Japan .................. 62-282064

[51] Int. Cl.$^5$ ........................... A61K 31/505
[52] U.S. Cl. ................................. 514/258
[58] Field of Search ................ 514/258, 826

[56] References Cited

U.S. PATENT DOCUMENTS 4,122,274  10/1978  Juby ..................... 544/282

Primary Examiner—Leonard Schenkman
Attorney, Agent, or Firm—McGlew & Tuttle

[57] ABSTRACT

An aqueous preparation for the treatment of allergic diseases comprising 9-methyl-3-(1H-tetrazol-5-yl)-4H-pyrido[1,2-a]pyrimidin-4-one potassium salt, dibasic potassium phosphate and monobasic potassium phosphate. The aqueous preparation has no local irritation yet has physicochemical stability during long-term storage.

11 Claims, No Drawings

AQUEOUS PREPARATION OF 9-METHYL-3-(1H-TETRAZOL-5-YL)-4H-PYRIDO[1,2-A])PYRIMIDIN-4-ONE POTASSIUM SALT

BACKGROUND OF THE INVENTION

This invention relates to aqueous preparations containing an antiallergic drug. More particularly, it relates to aqueous preparations, such as nasal drops, eye drops and paints, i.e. medication paints, containing 9-methyl-3-(1H-tetrazol-5-yl) 4H-pyrido[1,2-a]pyrimidin-4-one potassium salt (hereinafter referred to as TBX).

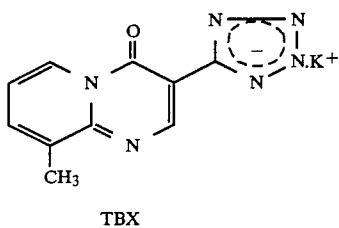

TBX

TBX is the compound described in Japanese Pat. Publication No. 50197/'85 (corresponding to U.S. Pat. No. 4,122,274) and is known to be effective in suppressing or preventing various symptoms of allergic reactions such as allergic bronchial asthma and allergic rhinitis. It is described in the literature that TBX has an inhibitory effect on a model for type I allergic reaction and suppresses the release of chemical mediators such as histamine and SRS-A (slow reacting substance of anaphylaxis) (Allergy, 33(9), p. 727 & 728, 1984). It is also described in the literature that TBX is useful for the treatment of gastritis and gastric ulcer owing to its protective effect on gastric cells (Gastroenterology, 88(5), p. 1354, 1985).

At present, commercially available antiallergic agents of the chemical mediator release suppression type are predominantly in the form of oral preparations which have systemic action for their object. However, this dosage form cannot necessarily be considered to be most suitable for patients (particularly infants) with allergic rhinitis, ophthalmia or dermatitis, partly because the incidence of side effects is rather high. Accordingly, it may safely be said that, in order to reduce the incidence of side effects and produce the drug effect more efficiently, useful dosage forms are topical preparations such as nasal drops for allergic rhinitis, eye drops for allergic ophthalmia, and paints for allergic dermatitis.

The primary object of the present invention is to provide aqueous preparations, such as nasal drops, eye drops and paints, i.e. medication paints, containing TBX which is an antiallergic agent.

Aqueous preparations must meet the requirements that they are sterile, they contain no foreign matter, the tonicity and pH thereof are not very different from those of the body fluid present at the site of application, no irritation is caused to the site of application, and they are physicochemically stable during long-term storage.

Although TBX is a water-soluble substance, aqueous solutions of TBX have poor storage stability because crystals tend to precipitate therefrom. For example, precipitation of crystals occurred in 10 days when the concentration of TBX was in the range of 0.02 to 2.0% (w/v), and in 12 days when it was 0.002% (w/v). In order to prevent the precipitation of crystals, solubilizing agents such as polyoxyethylene hydrogenated castor oil, polyoxyethylene sorbitan fatty acid ester, polyvinyl alcohol and glycerin were added. In all cases, however, precipitation of crystals occurred within 14 days. Moreover, conventional ophthalmic buffer solutions such as Hind-Goyan's, Gifford's and Palitzsch's buffer solutions ["The General Principles of Pharmacy (New Edition)", Nankodo, 1980, pp. 39-41] were used, but no satisfactory result could be obtained. The present inventors confirmed these facts on the basis of experiments conducted by themselves.

SUMMARY OF THE INVENTION

In view of the above-described problems, the present inventors have made an intensive study of aqueous preparations of TBX and have discovered that, when dibasic potassium phosphate and monobasic potassium phosphate are added to such preparations, no precipitation of crystals occurs even during long-term storage, the TBX does not undergo decomposition, and no irritation is caused to the site of application. The present invention has been completed on the basis of this discovery.

According to the present invention, an aqueous preparation preferably contains 0.05 to 0.5% (w/v) of TBX, 0.1 to 0.5% (w/v) of dibasic potassium phosphate and 0.005 to 0.2% (w/v) of monobasic potassium phosphate. If necessary, it can additionally contain antiseptics and isotonicity agents. The aqueous preparation of the present invention is preferably in the form of a nasal drop, an eye drop or a paint i.e. medication paint. However, the present invention can also be applied to liquid preparations such as injections, inhalations and ear drops.

DETAILED DESCRIPTION OF THE INVENTION

The aqueous preparation of the present invention should contain 0.05 to 0.5% (w/v) of TBX, 0.1 to 0.5% (w/v) of dibasic potassium phosphate and 0.005 to 0.2% (w/v) of monobasic potassium phosphate. If necessary, antiseptics, isotonicity agents and the like may be added thereto. The aqueous preparation of the present invention has very good storage stability in that no precipitation of crystals occurs even during long-term storage at room temperature or at low temperature which will be encountered in winter or in cold districts, and in that the TBX does not undergo decomposition. Moreover, its pH is stabilized in the range of 7.7 to 8.3. Accordingly, the aqueous preparation of the present invention is suitable for use as a nasal drop, eye drop or paint. Since nasal drops, eye drops and paints are repeatedly used by opening the container, it is preferable that they have good storage stability in the open state. The aqueous preparation of the present invention has been found to be stable in the open state, and this also demonstrates that it is suitable for use as a nasal drop, eye drop or paint.

Although any conventional antiseptics may be used in the aqueous preparation of the present invention, potassium sorbate and sodium dehydroacetate are preferred from the viewpoint of storage stability. Benzalkonium chloride, benzethonium chloride and 2-phenylethanol tend to induce precipitation of crystals.

Now, the results of experiments carried out under various prior art conditions are given below. More specifically, these experiments relate to cases [A] where TBX was dissolved in purified water alone, [B] where a solubilizing agent was added, and [C] where a conventional buffer solution (i.e., Hind-Goyan's, Gifford's or Palitzsch's buffer solution) was used.

The occurrence of precipitation of crystals was judged according to the visual inspection method described in the Pharmacopoeia of Japan. Specifically, samples are filled into tightly-stoppered glass container and allowed to stand. After a definite period of time, they were observed in a place illuminated with a white light source to an illuminance of 3,000 to 5,000 luxes. The plus (+) sign indicates that crystals separated out, and the minus (-) sign indicates that no precipitation of crystals was noted.

The term "sterile purified water" as will be used later refers to purified water that has been sterilized by heating in an autoclave at 121° C. for 20 minutes. [A] Where TBX was dissolved in purified water alone:

TBX was dissolved in sterile purified water at various concentrations. The resulting solutions were allowed to stand at room temperature and observed after 3, 10 and 12 days. The results thus obtained are shown in the following table 1.

TABLE 1

| TBX concentration, | Storage period (days) | | |
|---|---|---|---|
| %(w/v) | 3 | 10 | 12 |
| 1.0 | + | + | + |
| 0.5 | − | + | + |
| 0.2 | − | + | + |
| 0.02 | − | + | + |
| 0.002 | − | − | + |

[B] Where a solubilizing agent was added; 0.5 g of TBX and each of the listed solubilizing agents were dissolved in sterile purified water. This solution was brought to a pH of about 8.0 by the addition of 0.4 g of sodium citrate, and then adjusted to a total volume of 100 ml. The resulting 0.5% (w/v) TBX solutions were allowed to stand and observed. The results thus obtained are shown in the following table 2.

TABLE 2

| Solubilizing agent | Concentration of solubilizing agent, %(w/v) | Storage period (days) | | | |
|---|---|---|---|---|---|
| | | 1 | 3 | 7 | 14 |
| Polyoxyethylene hydrogenated castor oil | 0.5 | + | + | + | + |
| Polyoxyethylene sorbitan fatty acid ester | 0.5 | − | − | + | + |
| Polyvinyl alcohol | 0.5 | − | − | − | + |
| Glycerin | 10.0 | − | − | − | + |

[C] Where a conventional buffer solution was used:
(i) Hind-Goyan's buffer solution
0.40 g of monobasic sodium phosphate, 0.47 g of dibasic sodium phosphate and 0.43 g of sodium chloride were dissolved in sterile purified water. After the addition of 0.5 g of TBX, the total volume of this solution was adjusted to 100 ml. The resulting 0.5% (w/v) TBX solution was allowed to stand at room temperature or 5° C.
(Results)
At both room temperature and 5° C., crystals separated out instantly after the dissolution of TBX.
(ii) Gifford's buffer solution
1.24 g of boric acid, 0.74 g of potassium chloride and 2.12 g of sodium carbonate were dissolved in sterile purified water. After the addition of 0.20 g of TBX, the total volume of this solution was adjusted to 100 ml. The pH of the resulting 0.2% (w/v) TBX solution was 7.9. This solution was allowed to stand at room temperature or 5° C.
(Results)
Precipitation of crystals was clearly noted after three months' storage at room temperature and after one month's storage at 5° C.
(iii) Palitzsch's buffer solution
1.91 g of sodium borate and 1.24 g of boric acid were dissolved in sterile purified water. After the addition of 0.2 g of TBX, the total volume of this solution was adjusted to 100 ml. The pH of the resulting 0.2% (w/v) TBX solution was 8.2. This solution was allowed to stand at room temperature or 5° C.
(Results)
Precipitation of crystals was clearly noted after three months' storage at room temperature and after one month's storage at 5° C.

As described above, when TBX was dissolved in purified water, when each of the various solubilizing agents was added, and when each of the various conventional buffer solutions was used, crystals of TBX separated out instantly at the earliest or after three months at the latest, even in the tightly-stoppered state.

Next, several aqueous preparations in accordance with present invention were tested for storage stability in the tightly-stoppered state and in the open state and for local irritant properties.
(1) Storage stability
(Storage in the tightly-stoppered state)
TBX, dibasic potassium phosphate, monobasic potassium phosphate and, if necessary, potassium sorbate as an antiseptic were dissolved in sterile purified water so as to give their specified concentrations. The resulting aqueous preparations were placed in tightly-stoppered glass containers and stored at room temperature or 5° C. The results thus obtained are shown in Table 3. At the specified intervals of time, the occurrence of precipitation of crystals was judged according to the above-described visual inspection method. Thin-layer chromatography (TLC) was carried out by use of a plate having a thin layer of silica gel and a developing solvent comprising a mixture of methanol, benzene, acetone and aqueous ammonia (5:4:1:1). The observation was discontinued when precipitation of crystals was noted. Then, the samples were subjected to TLC.

TABLE 3

| Test No. | Concentration, %(w/v) | | | | pH |
|---|---|---|---|---|---|
| | TBX | Dibasic potassium phosphate | Monobasic potassium phosphate | Potassium sorbate | |
| 1 | 0.05 | 0.1 | 0.005 | 0.1 | 8.0 |
| 2* | 0.1 | 0.1 | 0.005 | 0.1 | 8.0 |
| 3 | 0.2 | 0.32 | 0.02 | — | 8.1 |
| 4 | 0.5 | 0.1 | 0.005 | 0.1 | 8.1 |
| 5 | 0.5 | 0.5 | 0.015 | — | 8.3 |

| Test No. | Temperature | Storage period (months) | | | | | | | | | TLC (number) of spots |
|---|---|---|---|---|---|---|---|---|---|---|---|
| | | 0.25 | 1 | 2 | 3 | 4 | 5 | 9 | 12 | 15 | |
| 1 | 5° C. | — | — | — | — | — | — | — | — | — | 1 |
| | R.T.** | — | — | — | — | — | — | — | — | — | 1 |
| 2 | 5° C. | — | — | — | — | — | — | — | — | — | 1 |
| | R.T. | — | — | — | — | — | — | — | — | — | 1 |
| 3 | 5° C. | — | — | — | — | — | — | — | — | — | 1 |
| | R.T. | — | — | — | — | — | — | — | — | — | 1 |

| | | | | | | | |
|---|---|---|---|---|---|---|---|
| 4 | 5° C. | − | − | − | + | | 1 |
| | R.T. | − | − | − | − | + | 1 |
| 5 | 5° C. | − | − | − | + | | 1 |
| | R.T. | − | − | − | − | + | 1 |

*0.3% (w/v) of potassium chloride was added as an isotonicity agent.
**Room temperature.

(Storage in the open state)

The samples of Test Nos. 1 and 2 in Table 3, which had been stored in the tightly-stoppered state for 15 months, were subsequently stored at room temperature with the glass containers uncapped. After the lapse of 10 days, no precipitation of crystals was noted. Moreover, TLC exhibited only one spot.

(2) Local irritant properties
(Irritation to the nasal mucosa)

0.05 ml of the nasal drop of Example 1 was sprayed into the nasal cavity of a rabbit three times a day. After this treatment was continued for a week, the epithelial tissue of the nasal cavity was observed under an optical and an electron microscope.

(Irritation to the ocular mucosa)

Ocular mucosa irritation tests were carried out by applying one drop of the eye drop of Example 2 to the anterior chamber of an eye of a rabbit four times a day and continuing this treatment for a week. Its effect was evaluated by measurement of the number of nictations and according to the Draiz method ("New Toxicity Tests—Methods and Evaluations", REALIZE Co., Feb. 28, 1987, p. 337).

(Irritation to the skin)

Skin irritation tests were carried out by applying 0.5 ml of the paint of Example 3 was applied to the back of a rabbit twice a day and continuing this treatment for 4 days. Its effect was evaluated according to the Federal Register method ("New Toxicity Tests—Methods and Evaluations", REALIZE Co., Feb. 28, 1987, p. 336).

(Results)

In all of the nasal mucosa, ocular mucosa and skin irritation tests, the treated animals showed no abnormality as compared with untreated controls.

Thus, the aqueous preparations of the present invention, which are formulated so as to contain 0.05 to 0.5% (w/v) of TBX, 0.1 to 0.5% (w/v) of dibasic potassium phosphate and 0.005 to 0.2% (w/v) of monobasic potassium phosphate, are very excellent preparations characterized in that no local irritation is caused, no precipitation of crystals occurs even after long-term storage at room temperature or in a cold place (at 5° C.), and the TBX does not undergo decomposition. Moreover, since they are also stable in the open state, they are especially useful as nasal drops, eye drops and paints which are repeatedly used by opening the container.

The aqueous preparations of the present invention are further illustrated by the following examples. However, these examples are not to be construed to limit the scope of the invention.

EXAMPLE 1

1.0 g of TBX, 3.0 g of dibasic potassium phosphate, 0.15 g of monobasic potassium phosphate and 1.0 g of potassium sorbate were dissolved in sterile purified water to make a total volume of 1,000 ml. The pH of the resulting solution was 8.1. This solution was filtered through a 0.45 um membrane filter to obtain a 0.1% (w/v) TBX solution. This solution was filled into a spray type container to produce a nasal drop.

EXAMPLE 2

1.0 g of TBX, 1.0 g of dibasic potassium phosphate, 0.05 g of monobasic potassium phosphate, 3.0 g of potassium chloride and 1.0 g of potassium sorbate were dissolved in sterile purified water to make a total volume of 1,000 ml. The pH of the resulting solution was 8.0. This solution was filtered through a 0.45 um membrane filter to obtain a 0.1% (w/v) TBX solution. This solution was filled into an eye dropper to produce an eye drop.

EXAMPLE 3

2.0 g of TBX, 3.0 g of dibasic potassium phosphate, 0.2 g of monobasic potassium phosphate and 0.1 g of sodium dehydroacetate were dissolved in sterile purified water to make a total volume of 1,000 ml. The pH of the resulting solution was 8.1. This solution was filtered through a 0.45 um membrane filter to obtain a 0.2% (w/v) TBX solution. This solution was filled into a sponge-capped plastic applicator bottle to produce a paint.

What is claimed is:

1. An antiallergic aqueous preparation containing an antiallergically effective amount of 0.05 to 0.5% (w/v) of 9-methyl-3-(1H-tetrazol-5yl)-4H-pyrido pyrimidin-4-one potassium salt, 0.1 to 0.5% (w/v) of dibasic potassium phosphate and 0.005 to 0.2% (w/v) of monobasic potassium phosphate.

2. An aqueous preparation as claimed in claim 1 which is in the form of a nasal drop.

3. An aqueous preparation as claimed in claim 1 which is in the form of an eye drop.

4. An aqueous preparation as claimed in claim 1 which is in the form of a medication paint.

5. Method of suppressing or preventing symptoms of allergic reaction in a subject comprising administering to the subject an antiallergically effective amount of the aqueous preparation of claim 1.

6. Method of claim 5 wherein the preparation is nasally administered in the form of a nasal drop.

7. Method of claim 5 wherein the preparation is administered to the eye in the form of an eye drop.

8. Method of claim 5 wherein the preparation is administered to a topical site in the form of a medication paint.

9. Method of claim 5 wherein the allergic reaction is allergic rhinitis and the preparation is nasally administered.

10. Method of claim 5 wherein the allergic reaction is allergic ophthalmia and the preparation is administered to the eye.

11. Method of claim 5 wherein the allergic reaction is allergic dermatitis and the preparation is administered to the skin.

* * * * *